United States Patent

Schmitt et al.

[11] Patent Number: 5,865,745
[45] Date of Patent: *Feb. 2, 1999

[54] REMOTE HEALTH CARE INFORMATION INPUT APPARATUS

[75] Inventors: Eric L. Schmitt, Honeoye; Michael K. Rogers, Mendon, both of N.Y.

[73] Assignee: Eastman Kodak Company, Rochester, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 757,364

[22] Filed: Nov. 27, 1996

[51] Int. Cl.$^6$ ......................................................... A61B 5/00
[52] U.S. Cl. ............................ 600/407; 128/920; 128/897; 250/580
[58] Field of Search .................................. 128/653.1, 920, 128/922, 924, 897; 395/924; 250/580, 584; 600/407

[56] References Cited

U.S. PATENT DOCUMENTS

| | | |
|---|---|---|
| 4,641,242 | 2/1987 | Kimura . |
| 4,991,091 | 2/1991 | Allen . |
| 5,235,510 | 8/1993 | Yamada et al. . |
| 5,270,530 | 12/1993 | Godlewski et al. ................. 250/208.1 |
| 5,311,032 | 5/1994 | Montoro et al. ......................... 250/584 |
| 5,315,505 | 5/1994 | Pratt et al. . |
| 5,343,869 | 9/1994 | Pross et al. .............................. 128/700 |
| 5,376,806 | 12/1994 | Hejazi . |
| 5,410,471 | 4/1995 | Alyfuku et al. . |
| 5,418,355 | 5/1995 | Weil . |
| 5,431,161 | 7/1995 | Ryals et al. .......................... 128/653.1 |
| 5,513,101 | 4/1996 | Pinsky et al. ........................... 364/401 |
| 5,546,942 | 8/1996 | Zhang .................................. 128/653.1 |
| 5,551,428 | 9/1996 | Godlewski et al. .................. 128/653.1 |
| 5,592,374 | 1/1997 | Fellegara et al. ....................... 395/203 |
| 5,630,664 | 5/1997 | Farrelly .................................. 128/695 |
| 5,666,953 | 9/1997 | Wilk ..................................... 128/653.1 |

*Primary Examiner*—Marvin M. Lateef
*Assistant Examiner*—Shawna J. Shaw
*Attorney, Agent, or Firm*—William F. Noval

[57] ABSTRACT

A health care information input apparatus comprising:
  a substantially rectangular housing having a front wall;
  a computer having memory mounted in said housing;
  a touch screen mounted on said front wall of said housing and connected to said computer;
  a bar code scanner mounted in said housing and having a scanning face which is mounted on said front wall of said housing adjacent to said touchscreen, said bar code scanner connected to said computer; and
  a network interface socket mounted on said housing and connected to said computer;
  wherein information input at said touch screen and at said bar code scanner are stored in said computer memory for transmission via said network interface.

6 Claims, 22 Drawing Sheets

Body Part

| | | | | |
|---|---|---|---|---|
| Adult Chest | Pelvis | T-Spine | Elbow | Tibia/Fibula |
| Portable Chest | Skull | LS-Spine | Humerus | Knee |
| Ped Chest | Facial Bones | Hand | Shoulder | Femur |
| Adult Abdomen | Nasal Bones | Wrist | Foot | Hip |
| Red Abdomen | C-Spine | Forearm | Ankle | Pattern |

Other

DONE

FIG. 15

Position

DONE

| Supine | Prone |
|--------|-------|
| Erect | Decub |
| Semi-Erect | Other |

FIG. 17

Orientation
Lengthwise 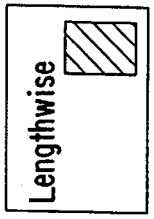   Crosswise 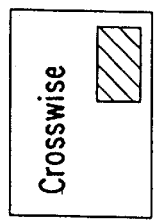
DONE
FIG. 18

| PROJECTION | BODY PART | POSITION | DISTANCE | KVP | MAS | ORENTATION |
|---|---|---|---|---|---|---|
| AP | CHEST | SUPINE | 40 | 50 | 1.25 | |
| LATERAL | SKULL | SEMI-ERECT | 42 | 60 | 1.5 | |
| RLD | ABDOMEN | ERECT | 45 | 70 | 2.5 | |
| LLD | CSPINE | | 50 | 80 | 3.2 | COMMENTS |
| X TABLE | PELVIS | | 72 | 85 | 50 | NONE |
| | EXTREMITY | | | | 80 | |

Set Date & Time

Current Date

Month  Day  Year
 01    15   1997

Current Time

Hour  Minute  Seconds
 03    22     17

DONE

Reset

Apply

Configuration

HIS/RIS Connection
○ Connected
○ Not Connected

Main Menu Config
○ With Technique
○ Without Technique

Requisition ID
○ Active
○ Inactive

Languages
○ English
○ French
○ German
○ Italian

DONE

FIG. 28

REMOTE HEALTH CARE INFORMATION INPUT APPARATUS

FIELD OF THE INVENTION

This invention relates in general to health care information and imaging systems and relates more particularly to a remote health care information input apparatus which is networked with a storage phosphor radiography system.

BACKGROUND OF THE INVENTION

In conventional film/screen radiography, the radiology procedure can follow the following scenario. 1. A requisition is filled out by a radiologist (or other health care professional) ordering a specific x-ray exam to be performed on a patient. The requisition is sent to the radiology department. 2. A technologist takes the requisition, one or more x-ray film cassettes, and positions the patient at an x-ray source. 3. The technologist performs the exam and the x-ray film(s) is exposed to x-rays which have been projected through a body part(s) of the patient. 4. The requisition is taped to the cassette and the exposed film is taken to a dark room to be developed. 5. At the darkroom a preprinted information card is flashed on to the film. Such information includes the patient name, patient ID number, patient birth date, health care facility name, current time and date, etc. 6. The film is processed and the technologist verifies that a good image has been recorded. 7. A sticker is applied to the film which records the date, time of exposure, exposure technique (kilovolts, milliamps, distance). 8. The finished x-ray film(s) are placed on a light box for review and diagnosis by a radiologist or physician.

Because of the inherent disadvantages of conventional radiography (as outlined above) in the acquisition, storage and transmission of patient x-ray images, a digital storage phosphor radiography system has come into use. In such a system, a storage phosphor contained in a cassette, is exposed to an x-ray image of a body part of a patient in the same manner as in conventional film-screen radiography. The exposed storage phosphor is read out in a storage phosphor reader to produce a digital x-ray image of the patient's body part. The digital x-ray image can then be processed to improve the image, displayed at a high resolution display station for review and diagnosis by a radiologist, transmitted to a remote location for display, stored in image storage, or sent to a radiographic printer for reproduction in visual form on film.

As with film-based radiography, storage phosphor radiography requires the matching of an x-ray image with a patient. In one known storage phosphor radiography system, patient information is entered into a workstation and is transferred to a magnetic card (See: U.S. Pat. No. 4,614,242, issued Feb. 3, 1987, inventor Kimura). After an exposure on a storage phosphor is made, a technologist places the cassette containing the exposed storage phosphor in a reader and transfers the corresponding patient information into the reader by swiping the patient's magnetic card through an associated magnetic card reader. Problems arise from double entry of patient information where such information has already been entered in a hospital information system when the patient entered the hospital, and from maintaining proper ordering of the storage phosphor cassettes and the patient information.

In another known storage phosphor radiography system (U.S. Pat. No. 5,418,355, issued May 23, 1995, inventor Weil), a hand-held bar code scanner is used to scan into the scanner bar code information relating to storage phosphor ID, patient ID, technologist ID, exam data, exposure technique, etc. The scanned information is then transferred to the storage phosphor reader at a bar code scanner download station located at the reader. Although this system is useful for the purposes for which it was intended, it would be desirable for the technologist not to have to carry a hand-held bar code scanner along with the storage phosphor cassettes, which can be quite bulky and heavy. Moreover, downloading of the information at a storage phosphor reader can be time consuming, where other technologists may be lined up wanting to do the same thing. It would also be desirable to reduce the amount of information that a technologist must enter for each cassette, if some of such information already exists in a HIS/RIS (Hospital Information System/Radiology Information System) that is accessible over a network.

SUMMARY OF THE INVENTION

According to the present invention, there is provided a solution to the problems discussed above.

According to an aspect of the present invention there is provided a health care information input apparatus comprising:

a substantially rectangular housing having a front wall;

a computer having memory mounted in said housing;

a touch screen mounted on said front wall of said housing and connected to said computer;

a bar code scanner mounted in said housing and having a scanning face which is mounted on said front wall of said housing adjacent to said touchscreen, said bar code scanner connected to said computer; and a network interface socket mounted on said housing and connected to said computer;

wherein information input at said touch screen and at said bar code scanner are stored in said computer memory for transmission via said network interface.

According to another aspect of the present invention there is provided a health care information system comprising:

a storage phosphor reader for converting a latent x-ray image stored in an exposed storage phosphor into a digital x-ray image, wherein said x-ray image represents a body part of a patient;

a workstation connected to and located near said storage phosphor reader for processing digital x-ray images from said reader; and a health care data input apparatus located remote from but connected to said workstation for inputting patient information and/or x-ray exam information relating to exposed storage phosphors to be read by said storage phosphor reader; said apparatus including:

a substantially rectangular housing having a front wall;

a computer having memory mounted in said housing;

a touch screen mounted on said front wall of said housing and connected to said computer; and a bar code scanner mounted in said housing and having a scanning face which is mounted on said front wall of said housing adjacent to said touchscreen, said bar code scanner connected to said computer;

wherein information relating to an exposed storage phosphor can be inputted by a user into said apparatus either by means of said touch screen interface or by means of said bar code scanner, and wherein said apparatus transmits said information to said workstation for storage, so that said information can be linked to a digital x-ray image read from said exposed storage phosphor by said storage phosphor reader.

Advantageous Effect

The present invention has the following advantages.

1. Patient information and/or x-ray exam information relating to an exposed storage phosphor may be entered remote from a storage phosphor reader but easily transmitted over a network link thereto.
2. A technologist carrying several exposed storage phosphor cassettes can scan a cassette ID barcode directly into a remote information input station without needing to carry a separate bar code scanner.
3. Patient information and/or x-ray exam information can be inputted into an information system either through a touch screen or a bar code scanner.
4. A user can scan a requisition ID bar code which causes the display of HIS/RIS information on a remote information input apparatus that has been downloaded from the HIS/RIS system to a storage phosphor radiography system central database.
5. A user can view limited patient information at a remote information input apparatus to be stored in a storage phosphor radiography system central database.
6. A user can enter x-ray exam information relating to a storage phosphor at a remote information input apparatus which is matched with a storage phosphor cassette at any storage phosphor reader on a networked system including the input apparatus.

DESCRIPTION OF THE DRAWINGS

FIGS. 11–22 are diagrammatic views of exemplary touch screen displays useful in explaining the present invention.

FIG. 23 is a perspective view of a barcode chart including barcodes for x-ray exam features and technique parameters.

FIGS. 24–28 are diagrammatic views of exemplary touch screen displays useful in explaining the setup feature of information input apparatus of the present invention.

DESCRIPTION OF THE PREFERRED EMBODIMENTS

Figure 1:
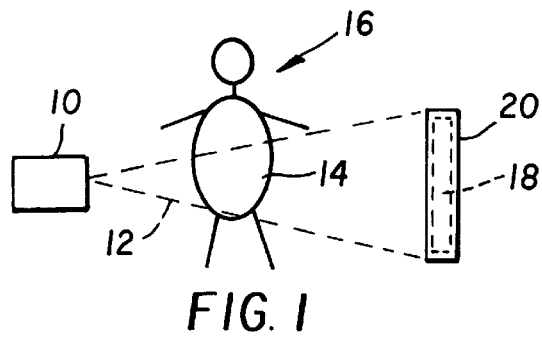
FIG. 1 is a diagrammatic view of an x-ray exposure of a storage phosphor.
Figure 2:
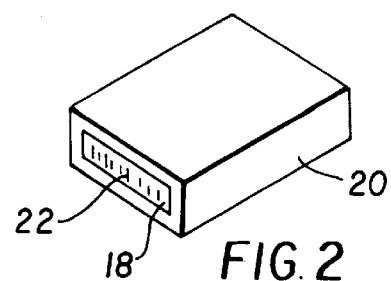
FIG. 2 is a perspective view of a storage phosphor cassette including a cassette ID barcode.

Referring now to FIG. 1, there is shown a diagrammatic view of an x-ray exposure exam. As shown, x-ray source 10 projects a beam of x-rays through body part 14 (e.g., abdomen) of patient 16. An x-ray image of the body part 14 is stored in storage phosphor 18 contained in cassette 20. As shown in FIG. 2 cassette 20 includes a storage phosphor ID bar code 22.

Figure 3:
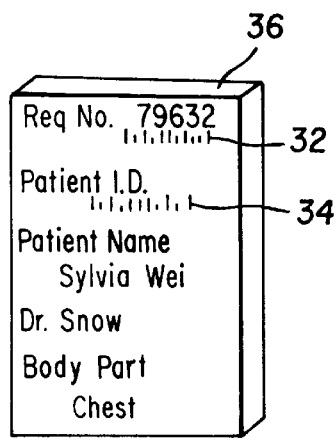
FIG. 3 is a perspective view of a requisition showing requisition ID barcode and patient ID barcode.
Figure 4:
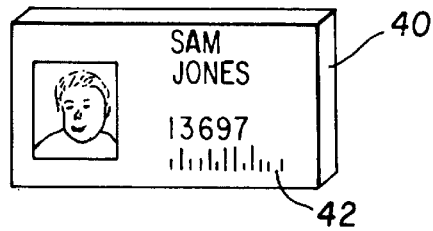
FIG. 4 is a perspective view of a technologist badge showing technologist ID barcode.

Before the x-ray exam is carried out, a technologist will have received a requisition to carry out specific x-ray exams on a patient. FIG. 3 shows a requisition sheet 30 having a requisition ID bar code 32 and a patient ID bar code 34, as well as other patient information and information relating to the x-ray exam to be carried out. The technologist who carries out the x-ray exam has an ID badge 40 (FIG. 4) which has a technologist ID bar code 42.

Figure 5:
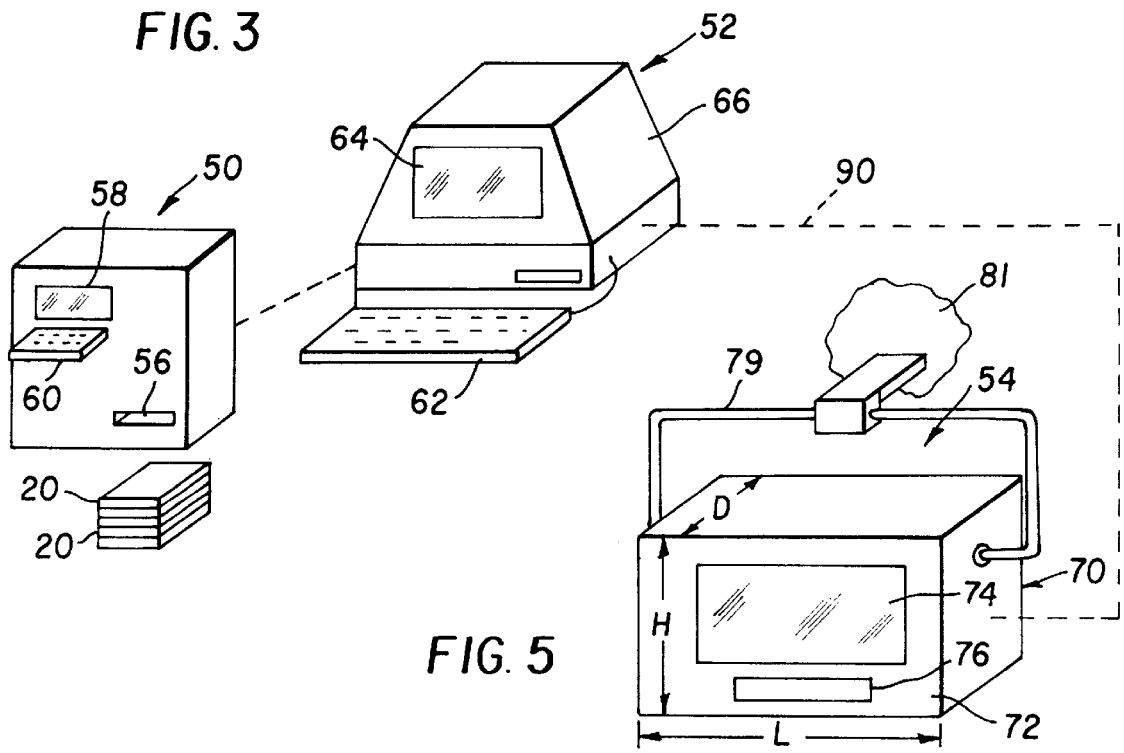
FIG. 5 is a perspective view of a health care information and imaging system according to an aspect of the present invention.

Referring now to FIG. 5, there is shown a storage phosphor radiography system incorporating the present invention. As shown, the system includes storage phosphor reader 50, image processing workstation 52, and remote health care information input apparatus 54. Reader 50 has a slot for receiving a storage phosphor cassette 20 containing an exposed storage phosphor 18. The cassette 20 can be manually loaded into slot 56 or can be loaded from a stack of cassettes 20 by a cassette autoloader (not shown). Reader 50 also has a display 58 and a user input keyboard 60.

Reader 50 scans an exposed storage phosphor 18 to convert a stored x-ray image in phosphor 18 into an electrical x-ray image which is digitized.

An exemplary storage phosphor reader is described in U.S. Pat. No. 5,376,806, issued Dec. 27, 1994, inventor Hejazi. The user input keyboard 60 (or other user input device, such as a touch screen) can be used to enter information relating to the x-ray image such as exam information, x-ray technique, etc. Reader 50 reads the cassette ID bar code 22 and links the entered information with the read x-ray image by means of the cassette ID.

The digital x-ray image produced by reader 50 is transmitted to image processing workstation 52 where it is stored. Workstation 52 includes a user input keyboard 62, a display 64, and (not shown) internally mounted in housing 66, a central processing unit (CPU), digital memory such as a magnetic hard drive, RAM, and ROM, etc. The memory stores image processing software routines which automatically process a digital x-ray image from reader 50. The user input 62 can be used to enter user selectable image processing parameters, as well as patient information relating to storage phosphor cassettes to be loaded into reader 50. Workstation 52 also functions as the central database for the system and when linked to a HIS/RIS system stores patient information from the latter system relating to storage phosphor cassettes processed by the storage phosphor radiography system.

According to one feature of the present invention, remote information input apparatus 54 includes a rectangular housing 70 having a depth dimension D which is substantially less than its length dimension L and its height dimension H. Housing 70 has a front wall 72. A touch screen user interface 74 is mounted on front wall 72. Also mounted on front wall 72 below touch screen 74 is the scanning face 76 of a bar code scanner 78.

Figure 6:
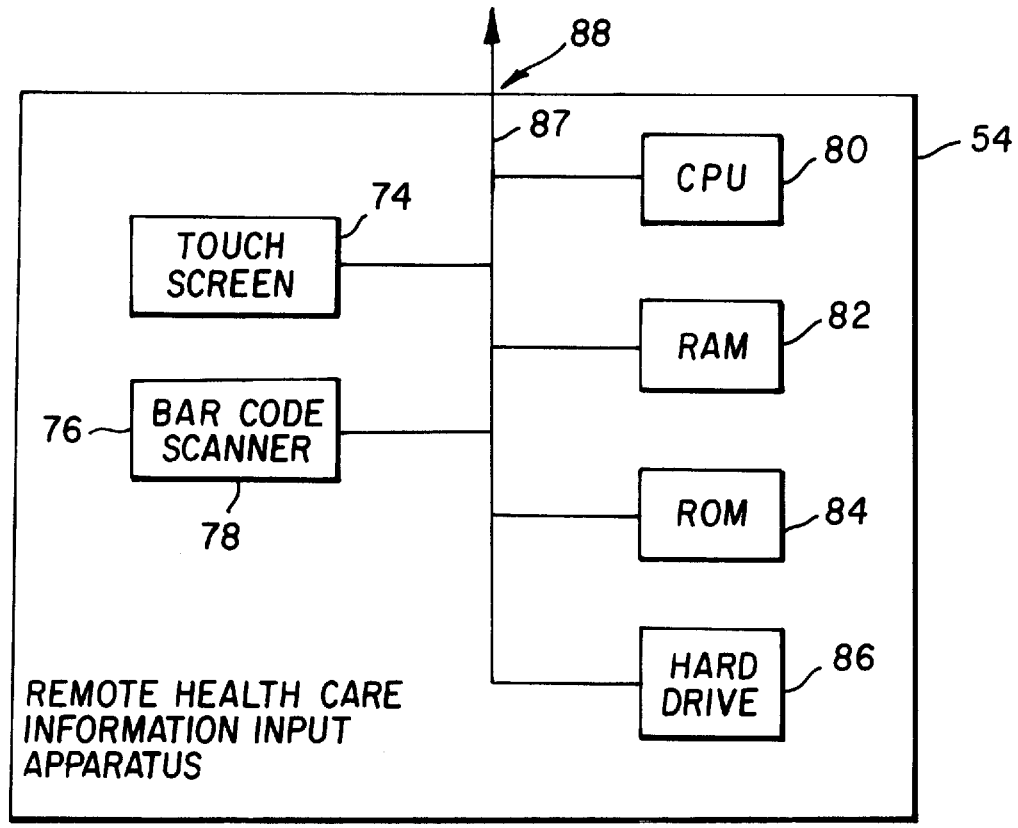
FIG. 6 is a block diagram of a health care information input apparatus according to another aspect of the present invention.

A block diagram of apparatus 54 is shown in FIG. 6. As shown, apparatus 54 includes touch screen user interface 74, bar code scanner 78 with scanning face 76, CPU 80, RAM 82, ROM 84, hard drive 86, connected by bus 87. An ethernet port 88 provides an ethernet link to workstation 52 via link 90. The operation of apparatus 54 will be described below.

Figure 7:
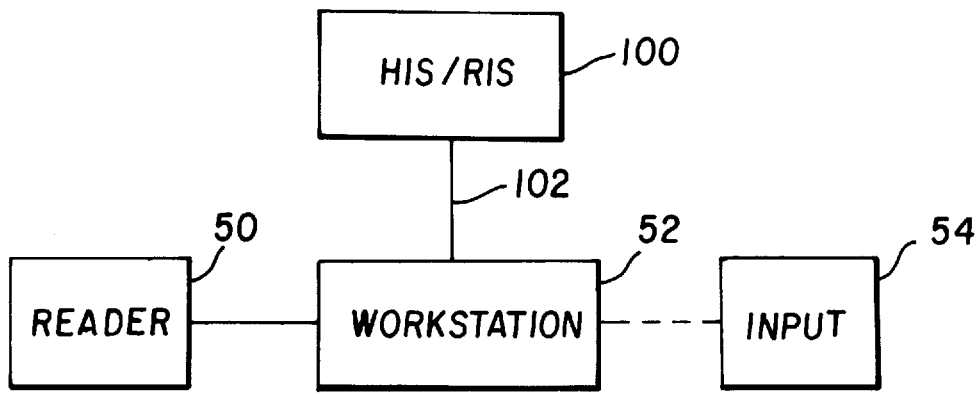
FIGS. 7–10 are block diagrams of systems incorporating the present invention.
Figure 8:
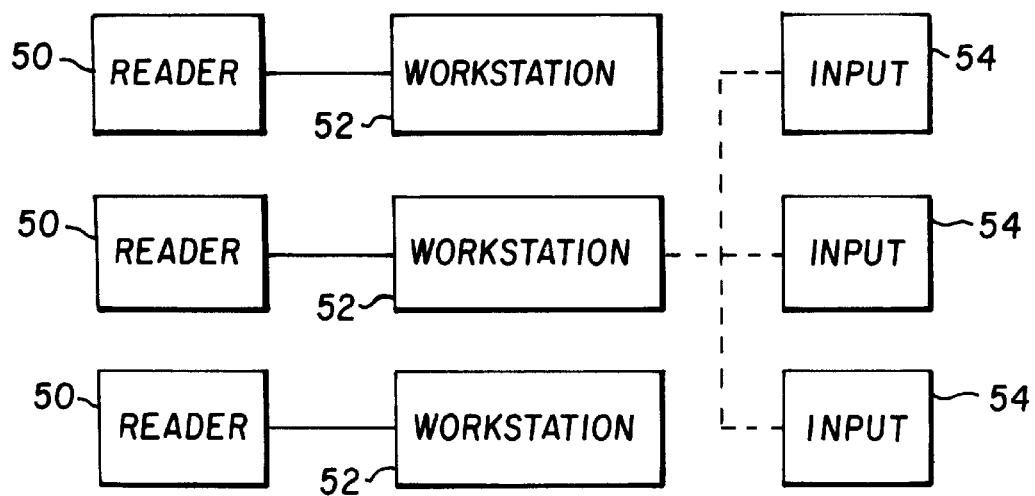
Figure 9:
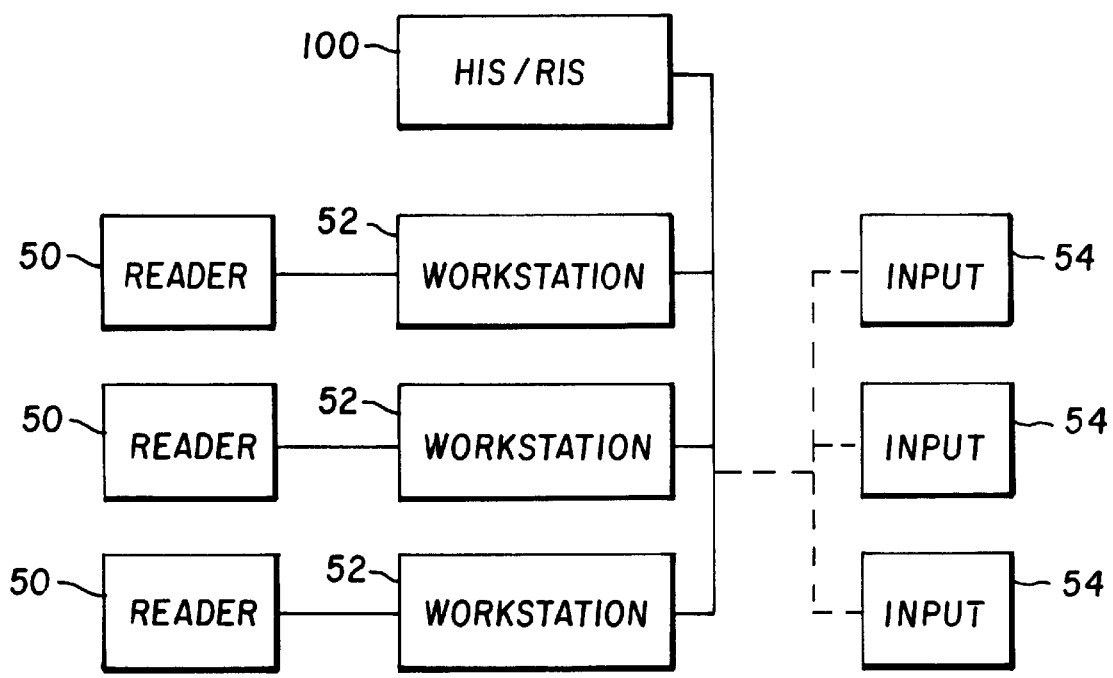

FIG. 5 shows one storage phosphor information imaging system according to the present invention. FIG. 7 shows another system where a HIS/RIS 100 is connected to the system of FIG. 5 by ethernet link 102. HIS/RIS 100 is a hospital information system (HIS) and/or a radiology information system (RIS) which stores all or some of the following information, requisition ID, patient ID, patient name, patient date of birth, patient body part to have x-ray exam. FIGS. 8 and 9 show expanded networks including several readers 50, workstation 52, and apparatus 54.

The operation of apparatus 54 will now be described. Information relating to requisition ID, technologist ID, patient ID, x-ray exam, and exam technique may be entered at apparatus 54 either by touch screen 74 or bar code scanner. If bar code scanner 78 is used, the patient ID barcode 34, and requisition ID bar code 32 can be scanned from requisition 30 (FIG. 3), the technologist ID bar code 42 can be scanned from the technologist badge 40 (FIG. 4), the cassette ID bar code 22 can be scanned from cassette 20 (FIG. 2), and exam info and exam technique can be scanned from a card 110 as shown in FIG. 23. The information entered into apparatus 54 is transmitted to workstation 52 over link 90.

Figure 10:
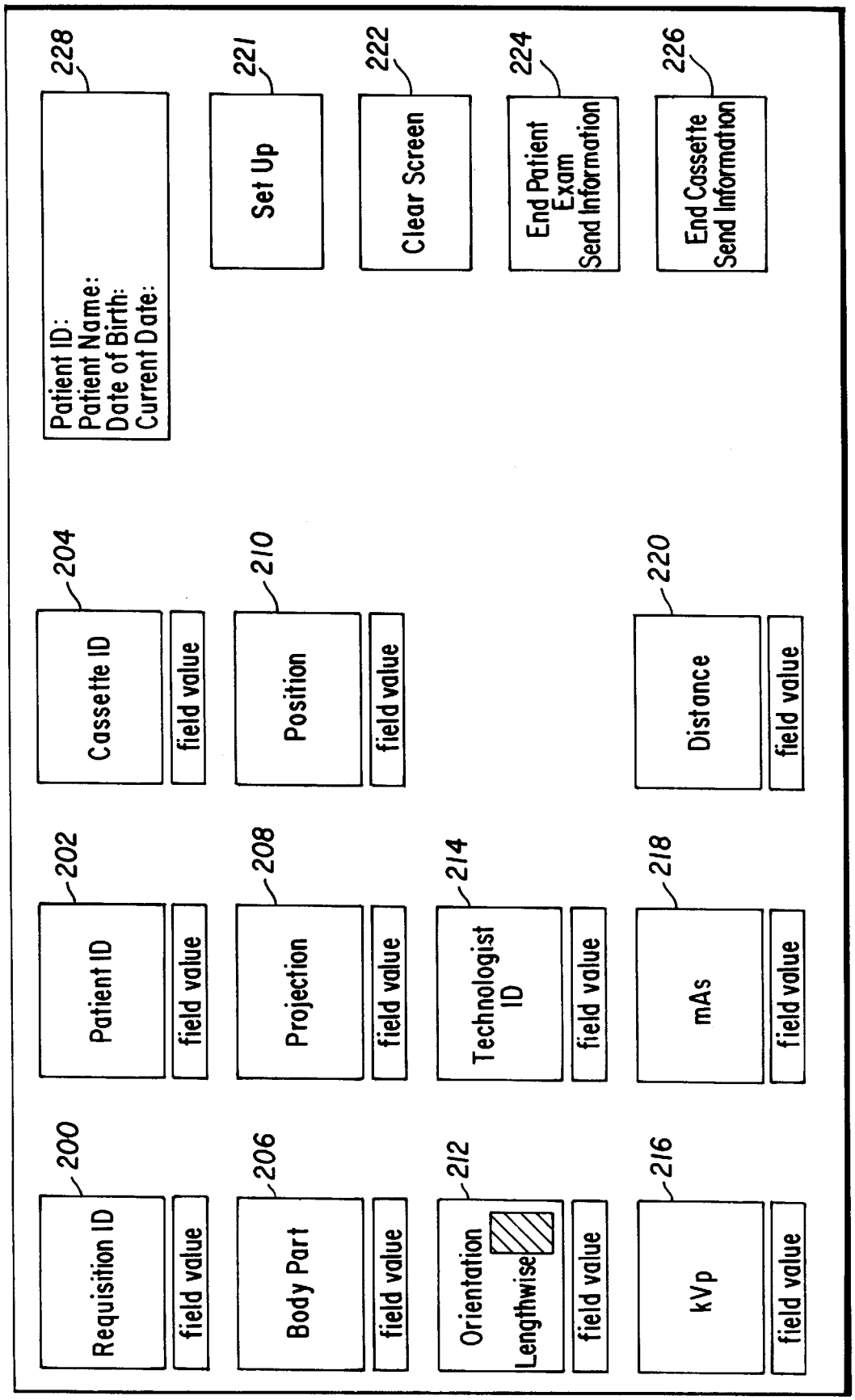

Some or all of this information can also be entered into apparatus 54 by touchscreen 74. FIGS. 10–22 are screens displayed on touch screen 64 which are useful in explaining entry of information. FIG. 10 shows the main screen with the following touch actuable fields: Requisition ID 200; Patient ID 202; Cassette ID 204; exam info—Body part 206, Projection 208, Position 210, Orientation 212; Technologist ID 214; and Exam technique info—kVp 216, mAs 218, Distance 220. Also included are Clear screen button 222, End patient Exam Send Info button 224, and End Cassette Send Information button 226. Display area 228 displays Patient ID, Patient Name, Date of Birth, Exam date, Exam Time.

Figure 11:
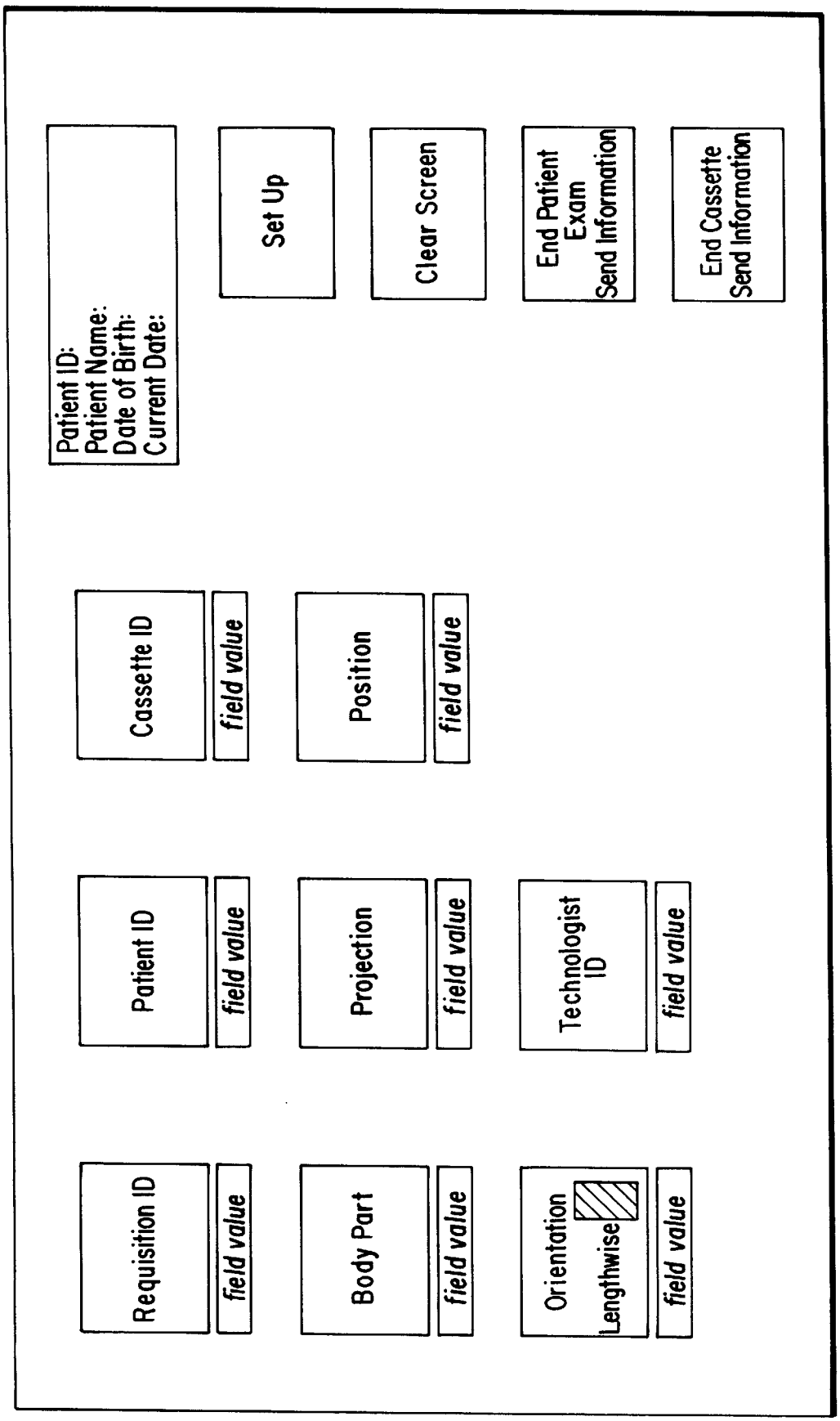
Figure 12:
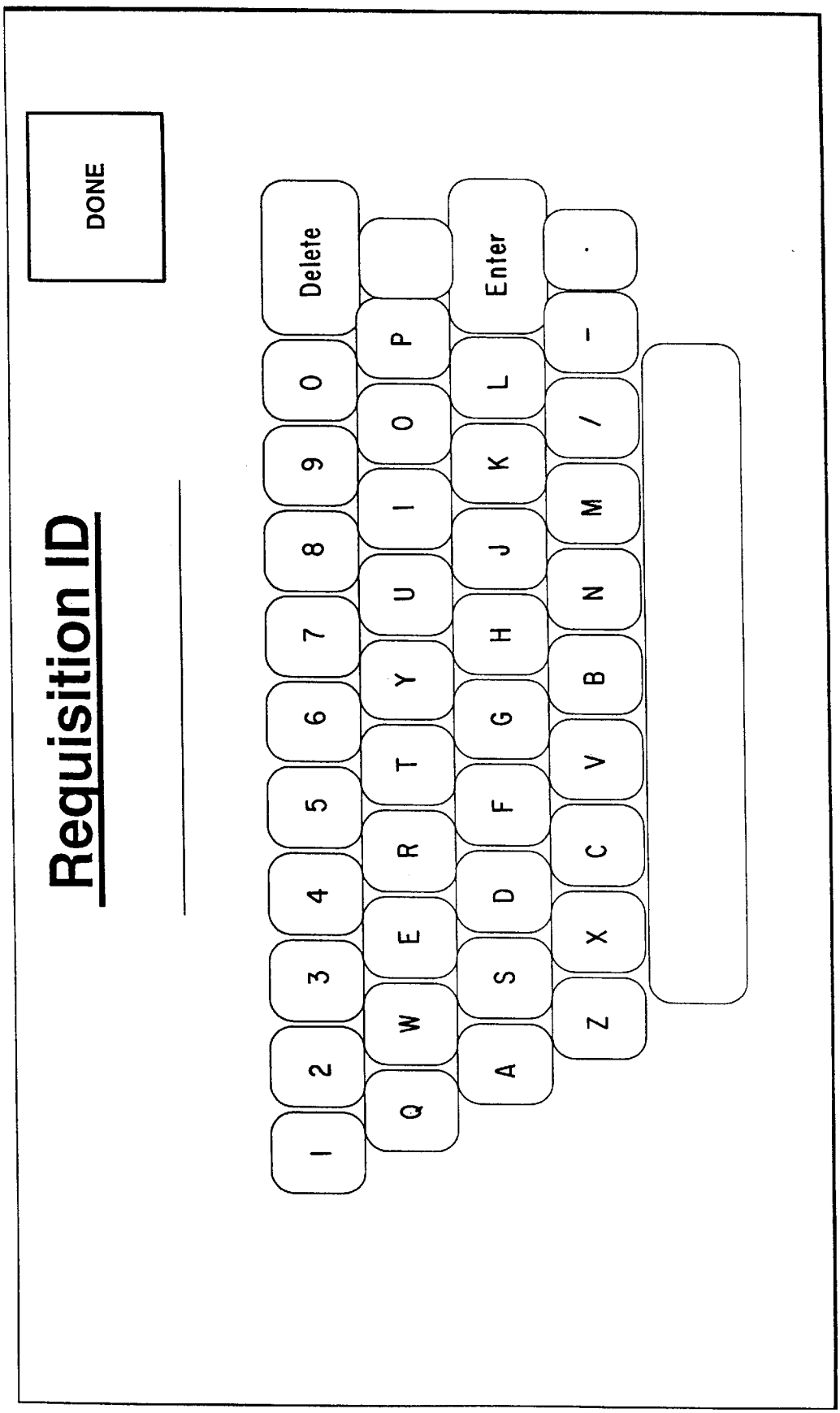
Figure 13:
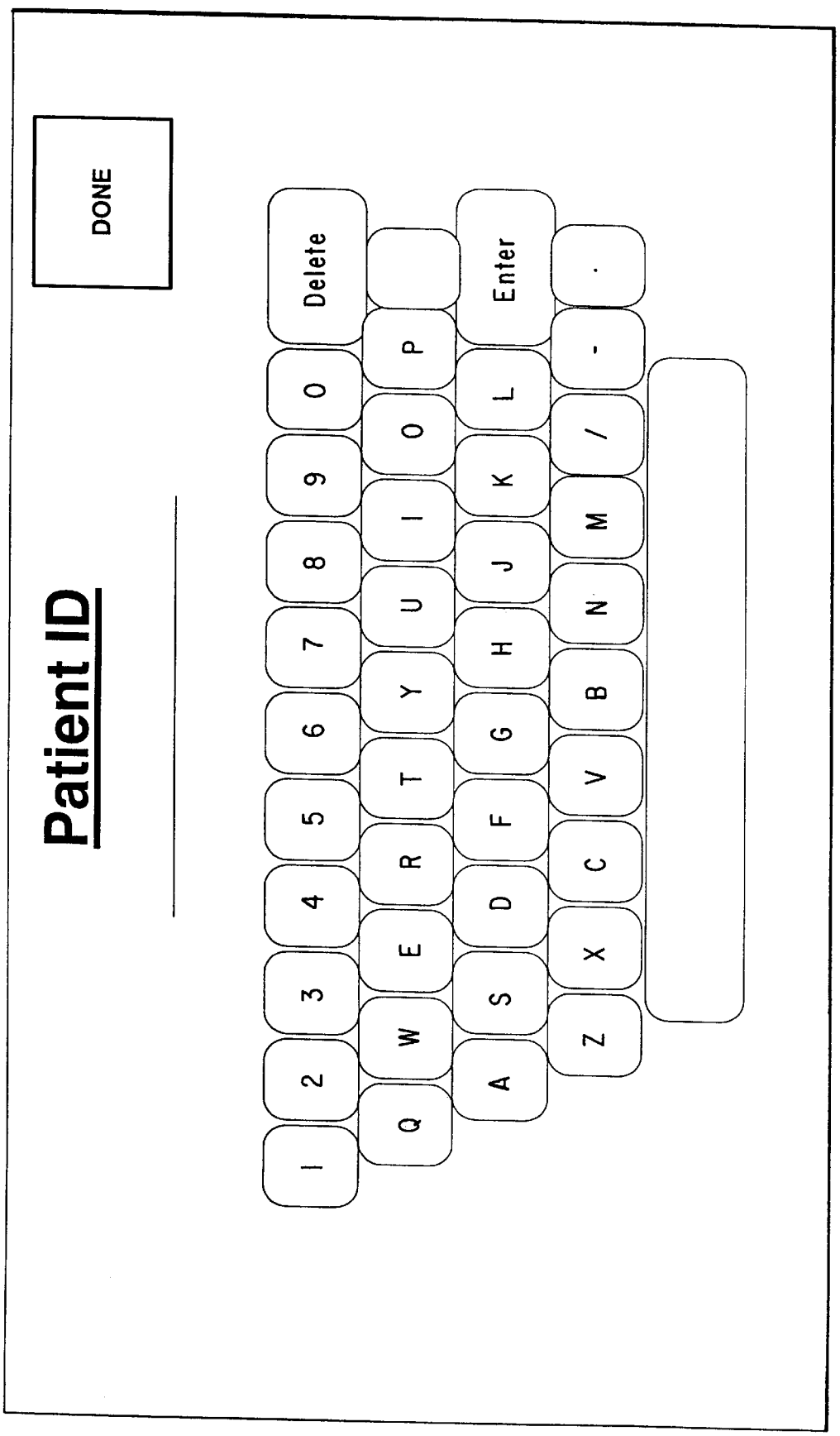
Figure 14:
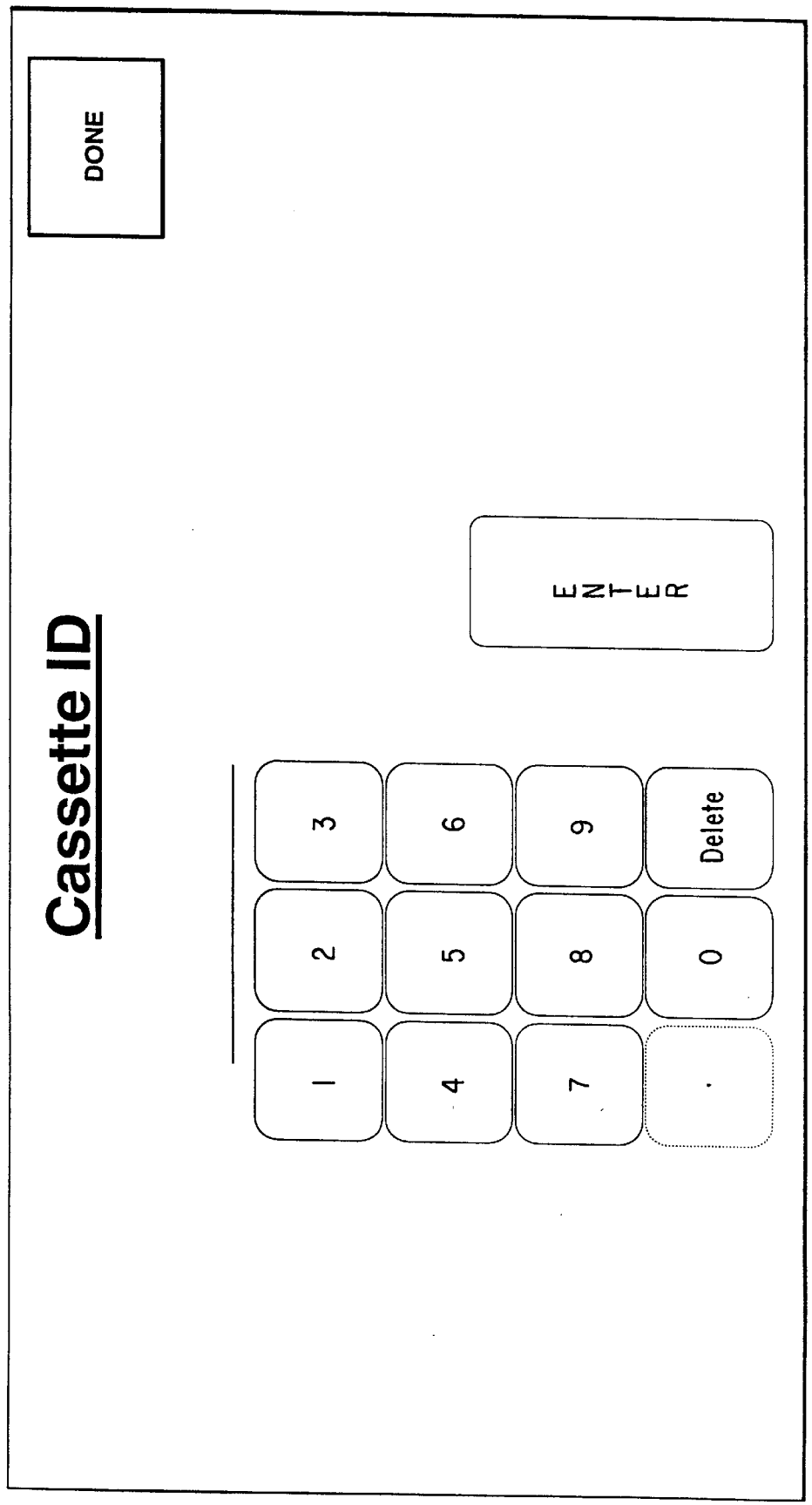
Figure 16:
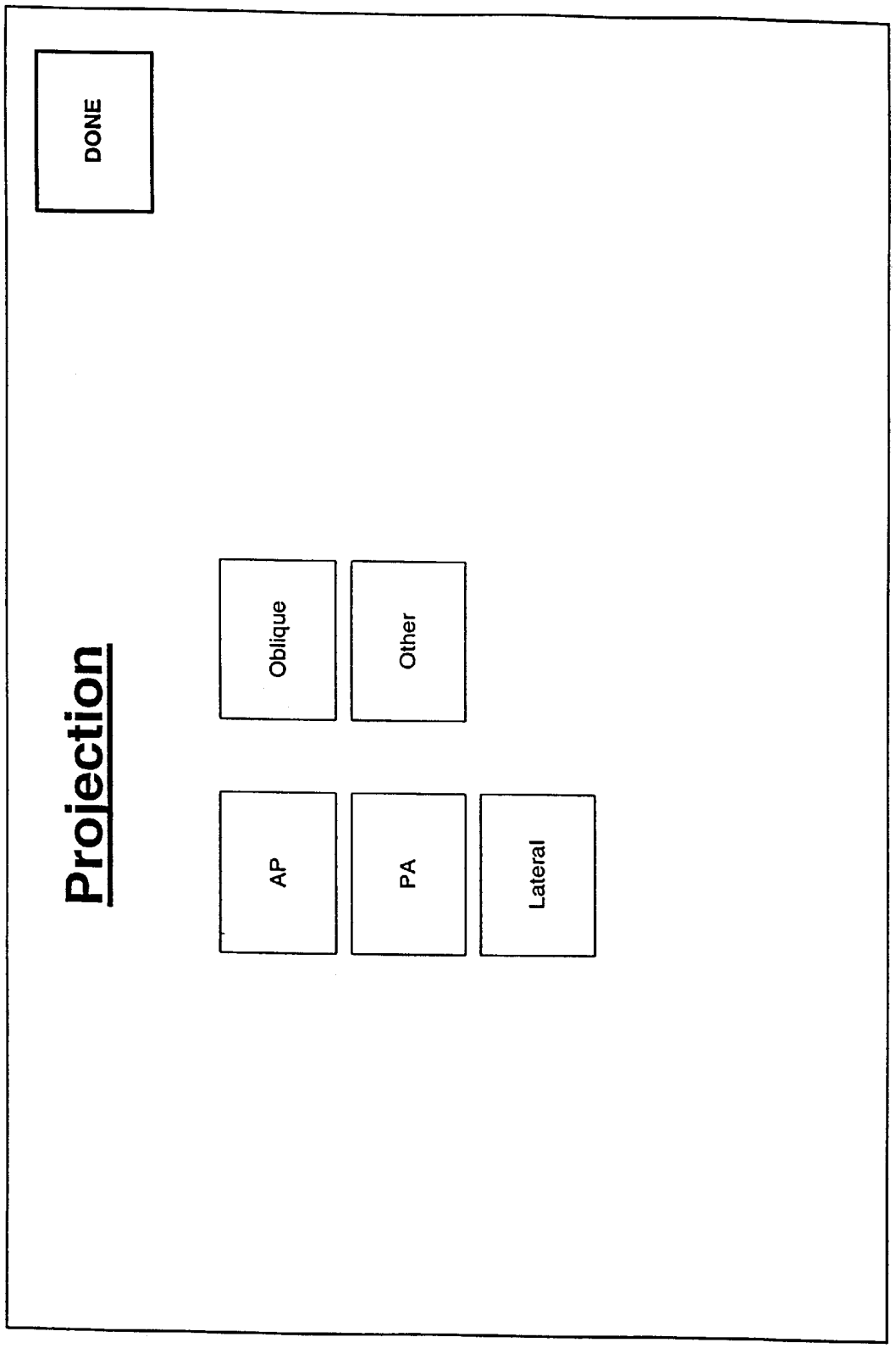
Figure 19:
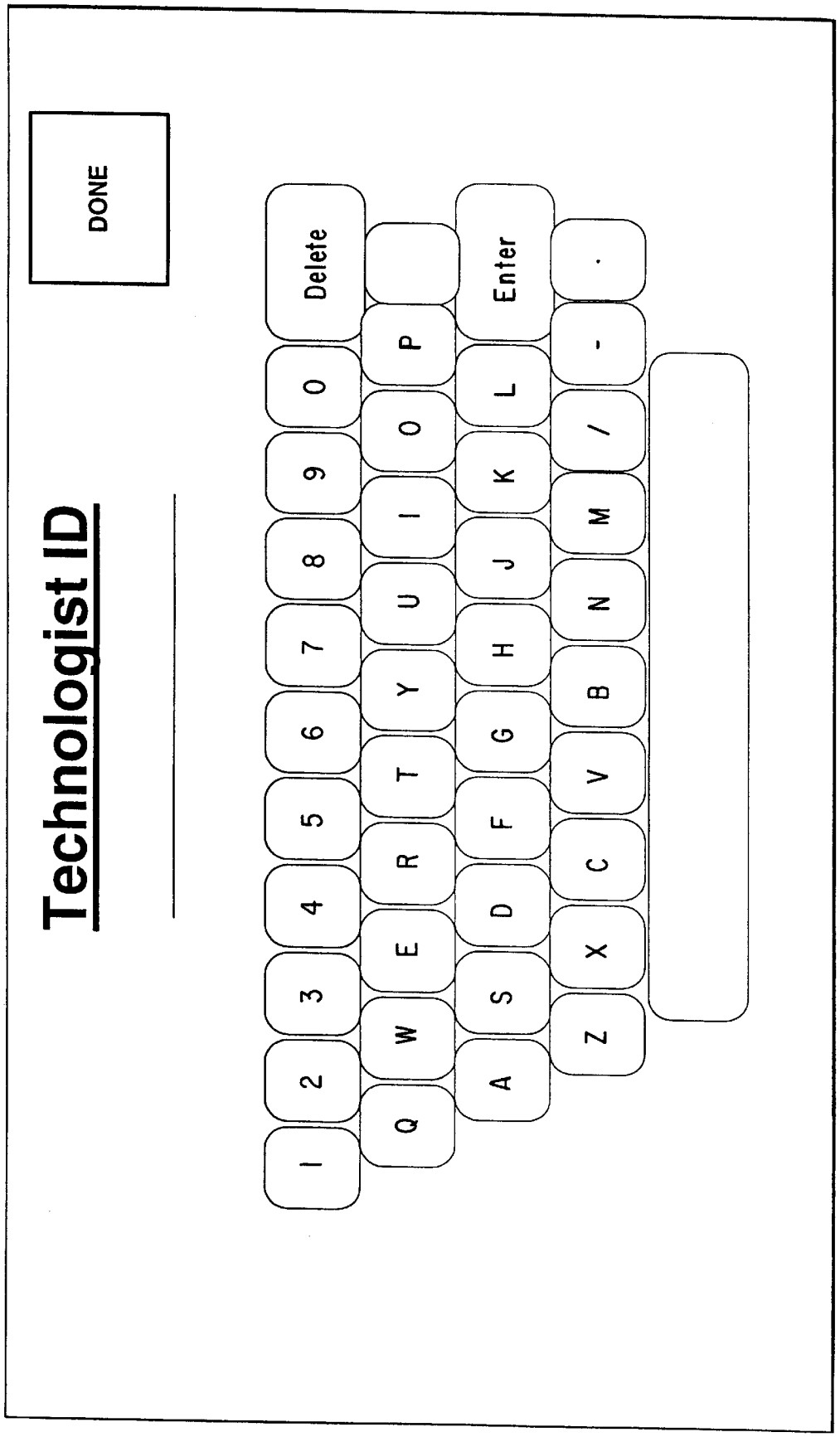
Figure 20:
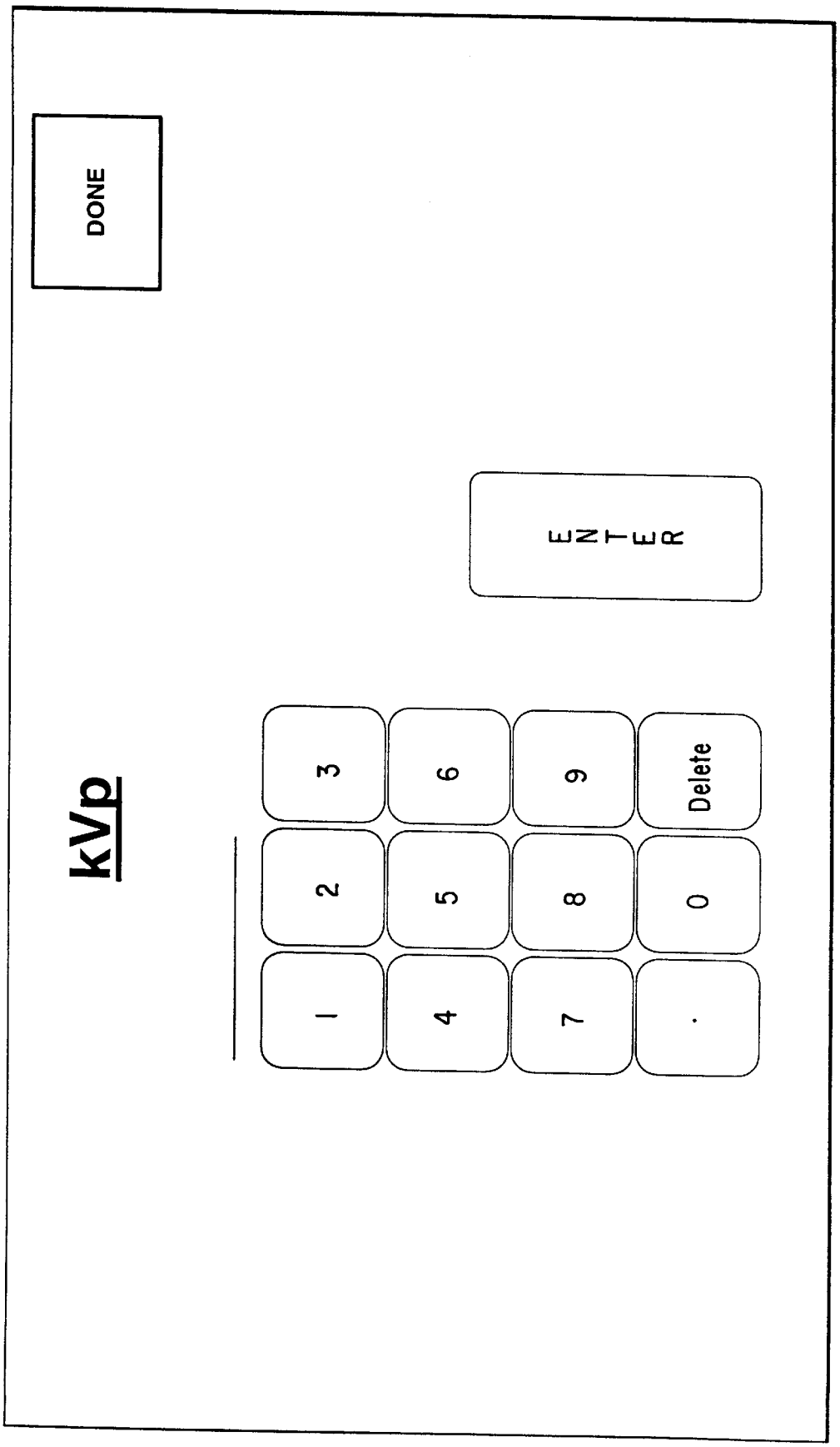
Figure 21:
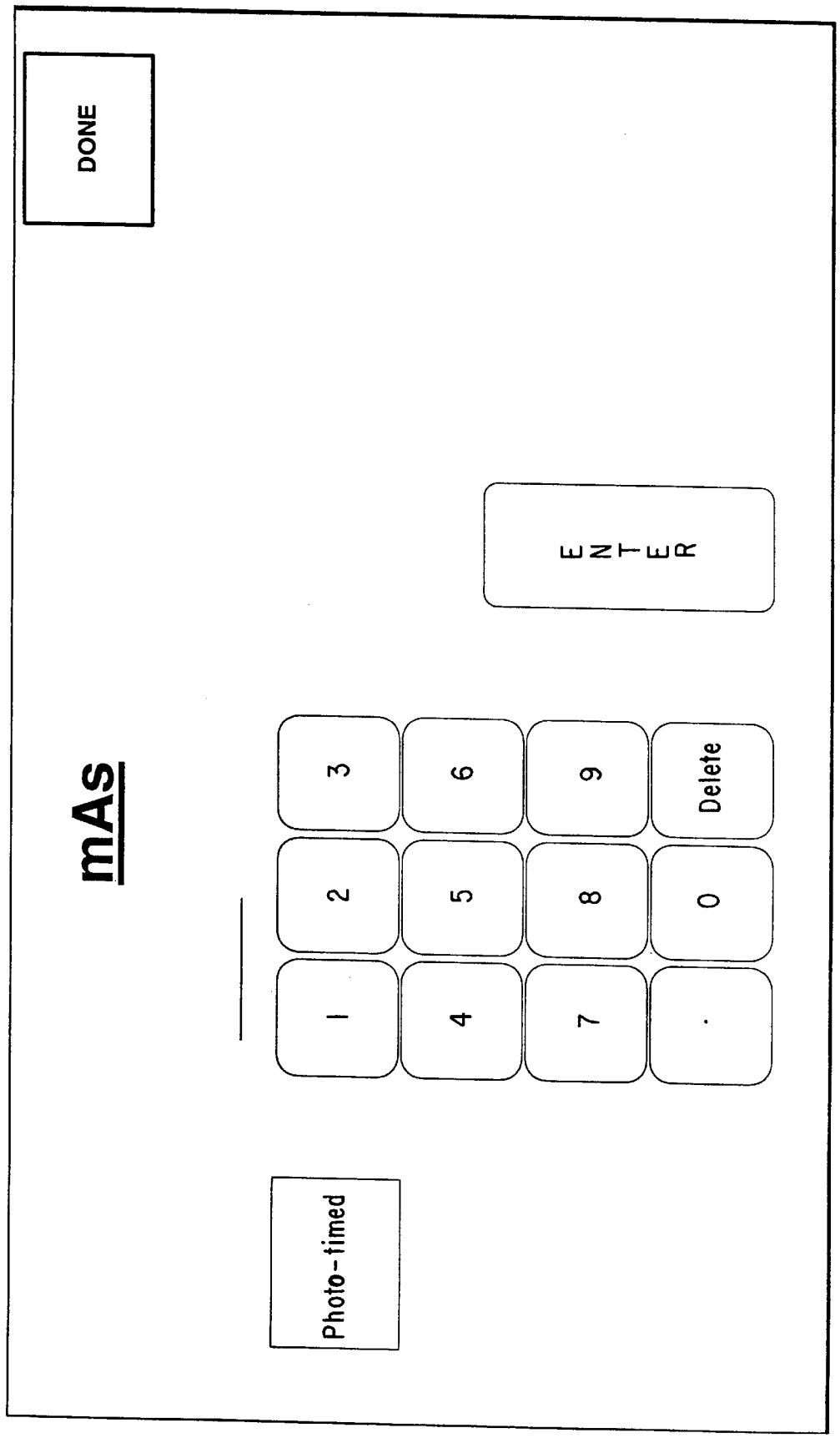
Figure 22:
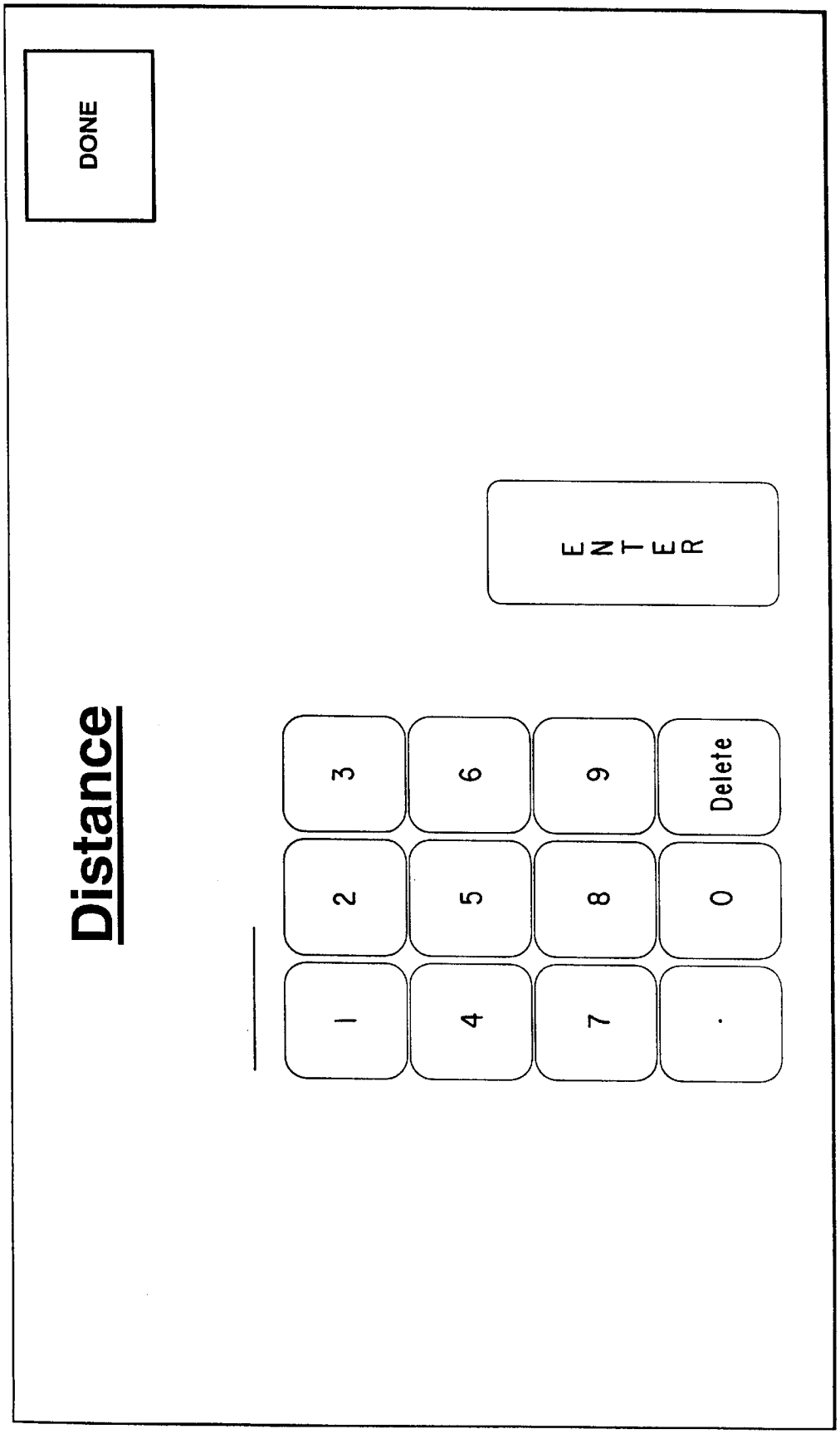
Figure 24:
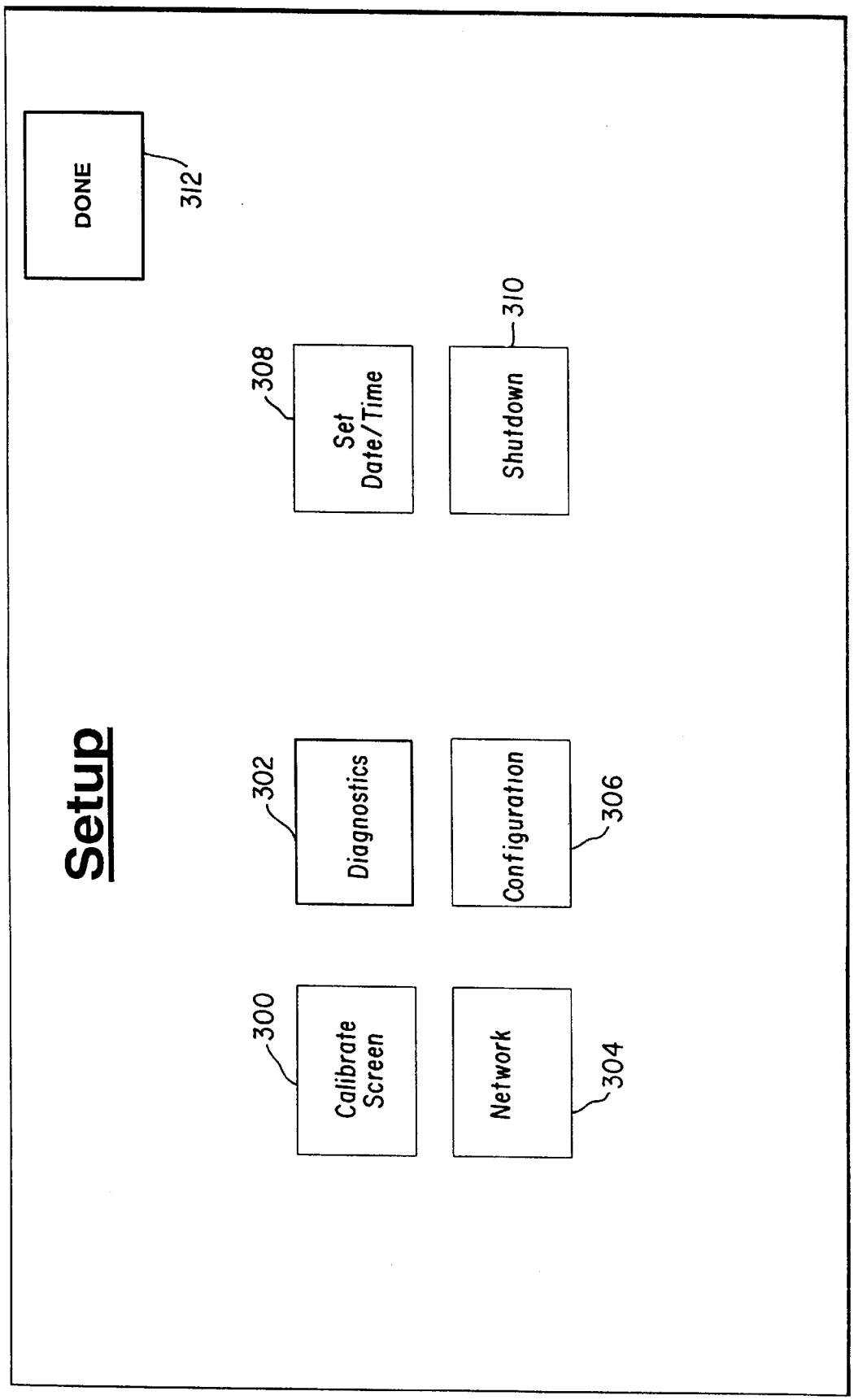
Figure 25:
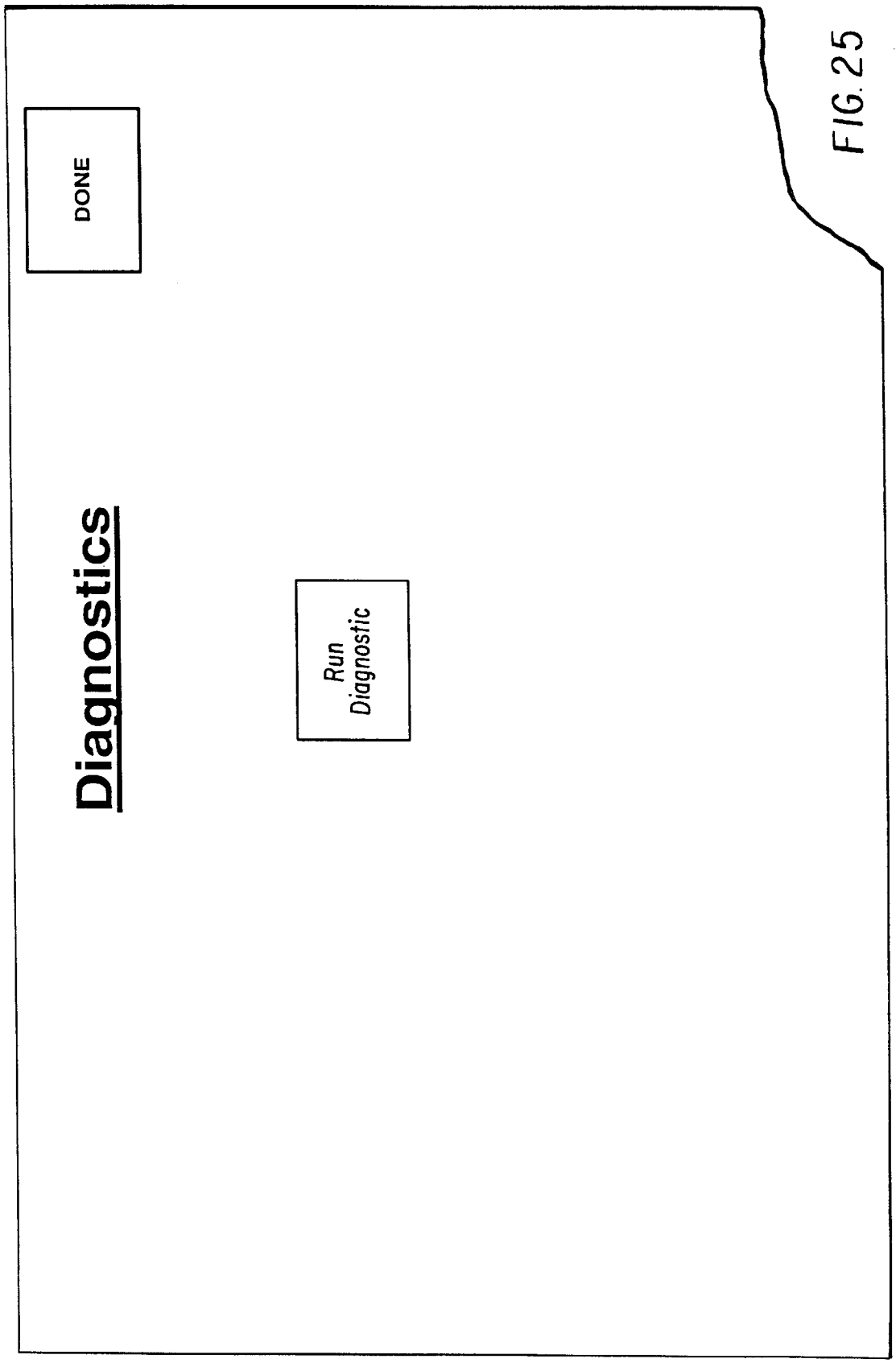
Figure 27:
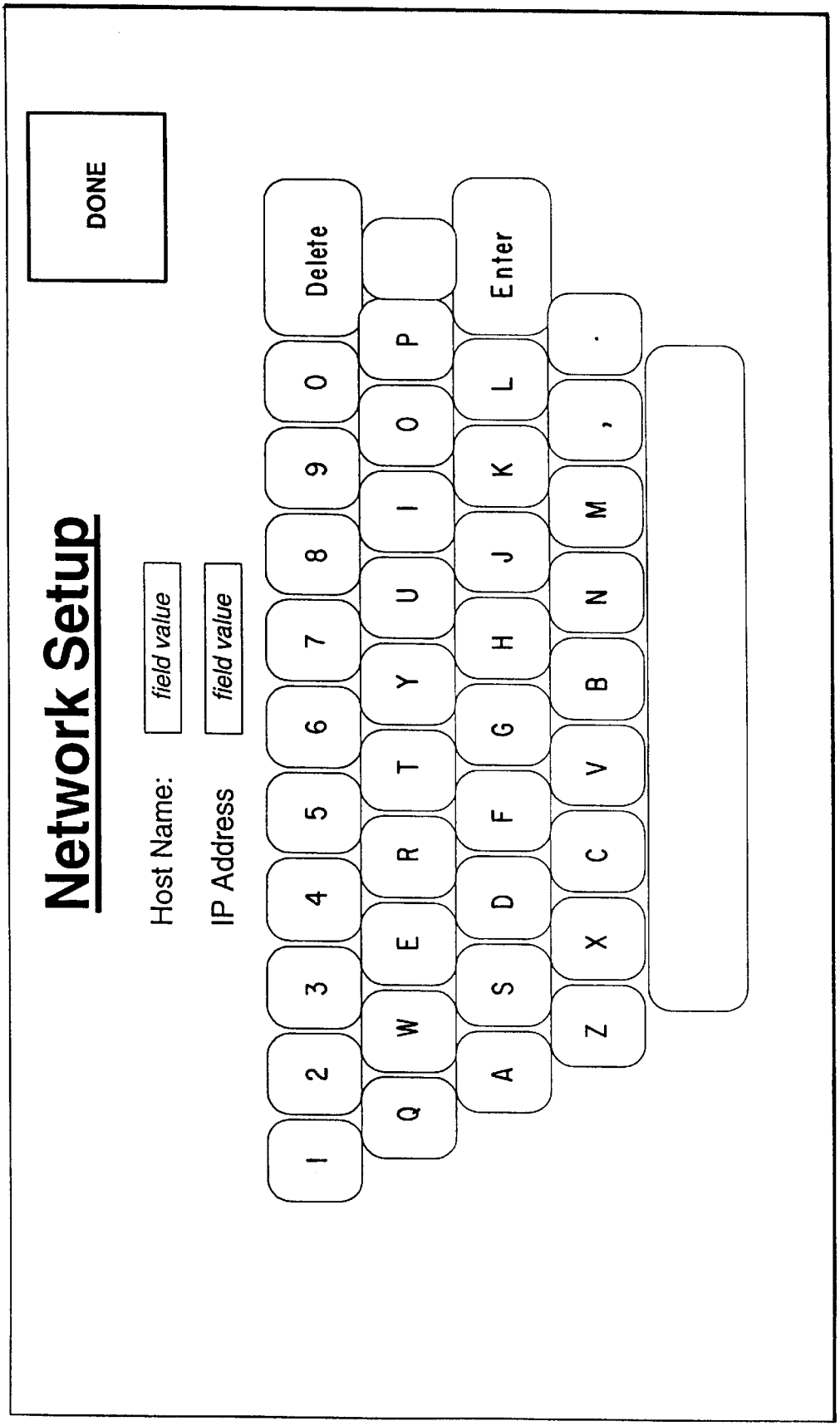

FIG. 11 also shows a main screen as in FIG. 10, but without the technique fields 216–218.

When one of the Requisition ID field 200, Patient ID field 202, Technologist Field ID 214 are touched, a QUERTY— style alphanumeric keyboard screen is displayed next (FIGS. 12, 13, 19, respectively) to enable entry of this information. When one of the Cassette ID field 204, kVp field 216, mAs field 218, Distance field 220 are touched, a numeric keypad screen is displayed next (FIGS. 14, 20, 21, 22, respectively) to enable entry of this information. When one of the Body Part field 206, Projection Field 208, Position field 210, Orientation field 212 are touched, an array of available options are displayed next (FIGS. 15, 16, 17, 18, respectively) to enable entry of this information. The information entered is then sent by link 90 to workstation 52 to be stored for subsequent linkage with a corresponding x-ray image when the storage phosphor storing the image is read by reader 50.

It will be understood that any item of information can be entered either by bar code scanner 76/78 or by touch screen 74.

In most cases, the user will approach information input apparatus with exposed cassettes and a requisition form for each cassette or set of cassettes for each patient. In a HIS/RIS configuration, the user will scan the requisition ID bar code from the requisition form, or enter it via the touch screen interface. In a non-HIS/RIS configuration, the user will scan the patient ID bar code or enter it via the touch screen. The user will then scan the cassette ID from the exposed cassette that corresponds to the requisition. The user will then make sure that the body part and projection are completed as well as any other pertinent fields. The user then presses the End Cassette/Send Information button to scan another cassette for the same requisition (same patient), or press the End Patient (send information) button to begin entering data for a new patient.

Although specific embodiments of the present invention have been described herein, it will be understood that variations and modifications can be made within the spirit and scope of the present invention.

PARTS LIST

10 x-ray source
12 x-ray beam
14 body part
16 patient
18 storage phosphor
20 cassette
22 storage phosphor ID bar code
30 requisition sheet
32 requisition ID bar code
34 patient ID bar code
40 ID badge
42 technologist ID bar code
50 storage phosphor reader
52 image processing workstation
54 remote health care information input apparatus
56 slot
58 display
60 user input keyboard
62 user input keyboard
64 display
66 housing
70 rectangular housing
72 front wall
74 touch screen user interface
76 scanning face
78 bar code scanner
79 bracket
80 CPU
81 wall
82 RAM
84 ROM
86 hard drive
87 bus
88 ethernet port
90 link
100 HIS/RIS
102 ethernet link
110 card
200 requisition ID button
202 patient ID button
204 cassette ID button
206 exam info—body part button
208 projection button
210 position button
212 orientation button
214 technologist id button
216 exam technique info—kVp button
218 mAs button
220 distance button
221 set up button
222 clear screen button
224 end patient exam send info button
226 end cassette send information button
228 display area button
300 calibrate screen button
302 diagnostics button
304 network setup button
306 configuration button
308 set date/time button
310 shutdown button
312 done button

What is claimed is:

1. A health care information input apparatus comprising:

a single substantially rectangular housing having a front wall;

a computer having memory mounted in said housing;

a touch screen mounted on said front wall of said housing and connected to said computer;

a bar code scanner fixedly mounted in said housing and having only a scanning face which is mounted on said front wall of said housing closely adjacent to and below said touchscreen, said bar code scanner connected to said computer; and a network interface socket mounted on said housing and connected to said computer;

wherein information input at said touch screen and at said bar code scanner are stored in said computer memory for transmission via said network interface.

2. The data input apparatus of claim 1 wherein said scanning face of said bar code scanner is mounted below said touch screen.

3. The apparatus of claim 1 wherein said housing has a depth dimension that is substantially less than its height and width dimensions.

4. The apparatus of claim 3 including means for mounting said apparatus on a wall.

5. The apparatus of claim 1 wherein said computer displays on said touch screen a sequence of screens which facilitate the entry into said computer of patient information and/or x-ray exam information relating to exposed storage phosphors.

6. A health care information system comprising:

a storage phosphor reader for converting a latent x-ray image stored in an exposed storage phosphor into a digital x-ray image, wherein said x-ray image represents a body part of a patient;

a workstation connected to and located near said storage phosphor reader for processing digital x-ray images from said reader; and a health care data input apparatus located remote from but connected to said workstation for inputting patient information and/or x-ray exam information relating to exposed storage phosphors to be read by said storage phosphor reader; said apparatus including:

a single substantially rectangular housing having a front wall;

a computer having memory mounted in said housing;

a touch screen mounted on said front wall of said housing and connected to said computer; and a bar code scanner fixedly mounted in said housing and having only a scanning face which is mounted on said front wall of said housing closely adjacent to and below said touchscreen, said bar code scanner connected to said computer;

wherein information relating to an exposed storage phosphor can be inputted by a user into said apparatus either by means of said touch screen interface or by means of said bar code scanner, and wherein said apparatus transmits said information to said workstation for storage, so that said information can be linked to a digital x-ray image read from said exposed storage phosphor by said storage phosphor reader.

* * * * *